United States Patent [19]

Jelich et al.

[11] Patent Number: 4,767,775
[45] Date of Patent: Aug. 30, 1988

[54] SUBSTITUTED PYRAZOLIN-5-ONES, COMPOSITION CONTAINING THEM, AND METHOD OF COMBATING FUNGI OR BACTERIA

[75] Inventors: Klaus Jelich, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 890,245

[22] Filed: Jul. 24, 1986

[30] Foreign Application Priority Data

Aug. 10, 1985 [DE] Fed. Rep. of Germany ....... 3528753

[51] Int. Cl.$^4$ .................... A61K 43/56; A61K 43/82; C07D 403/12; C07D 419/12
[52] U.S. Cl. .................... 514/379; 514/258; 514/269; 514/274; 514/312; 514/314; 514/341; 514/361; 514/363; 514/364; 514/365; 514/366; 514/369; 514/372; 514/373; 514/374; 514/375; 514/376; 514/378; 514/380; 514/404; 544/284; 544/298; 544/300; 544/310; 544/316; 544/317; 544/319; 544/333; 546/153; 546/155; 546/157; 546/176; 546/279; 548/126; 548/128; 548/129; 548/131; 548/132; 548/136; 548/143; 548/144; 548/169; 548/179; 548/183; 548/186; 548/203; 548/206; 548/207; 548/209; 548/213; 548/217; 548/221; 548/225; 548/226; 548/227; 548/228; 548/229; 548/232; 548/235; 548/240; 548/241; 548/243; 548/247; 548/364
[58] Field of Search ............... 548/364, 126, 128, 129, 548/131, 132, 136, 143, 144, 169, 179, 183, 186, 203, 206, 207, 209, 213, 217, 221, 225, 226, 227, 228, 229, 232, 235, 240, 241, 243, 247; 514/258, 269, 274, 312, 314, 341, 361, 363, 364, 365, 366, 369, 372, 373, 374, 375, 376, 378, 380, 404; 544/284, 298, 300, 310, 316, 317, 319, 333; 546/153, 155, 157, 176, 279

[56] References Cited

U.S. PATENT DOCUMENTS 4,666,933  5/1987  Jelich et al. .................... 548/365

FOREIGN PATENT DOCUMENTS 0048911  4/1982  European Pat. Off. ............ 562/598
0096903 12/1983  European Pat. Off. ............ 562/598
0166171  1/1986  European Pat. Off. ............ 548/364

OTHER PUBLICATIONS

Chemical Abstracts, vol. 97, No. 5, 1982, p. 569, abst No. 38878h.
Ber. dtsch. chem. Ges., 29, 249–259, (1896).
Liebigs Ann. Chem., 1976, 1380–1394.

*Primary Examiner*—Mary C. Lee
*Assistant Examiner*—Kurt G. Briscoe
*Attorney, Agent, or Firm*—Sprung Horn Kramer & Woods

[57] ABSTRACT

Microbicidal substituted pyrazolin-5-ones of the formula

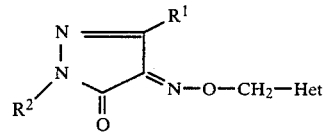

in which
$R^1$ and $R^2$ independently of one another each represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case optionally substituted oxiranylalkyl, aralkyl, heterocyclyl or aryl and
Het represents an optionally substituted heterocyclic radical.

Intermediates therefor of the formula

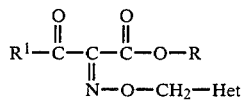

in which R is alkyl, are also disclosed.

11 Claims, No Drawings

SUBSTITUTED PYRAZOLIN-5-ONES, COMPOSITION CONTAINING THEM, AND METHOD OF COMBATING FUNGI OR BACTERIA

The invention relates to new substituted pyrazolin-5-ones, several processes for their preparation and their use as agents for combating pests.

It is already known that organic nitrogen compounds, such as, for example, zinc ethylene-1,2-bis-(di-thiocarbamate) have fungicidal properties (compare, for example, R. Wegler "Chemie der Pflanzenschutz- und Schädlingsbekämpfungsmittel" ("Chemistry of Plant Protection Agents and Agents for Combating Pests"), Springer Verlag Berlin, Heidelberg, New York 1970, Volume 2, page 65 et seq.).

The action of these compounds, however, is not always completely satisfactory in all fields of use, especially when low amounts and concentrations are applied.

New substituted pyrazolin-5-ones of the general formula (I)

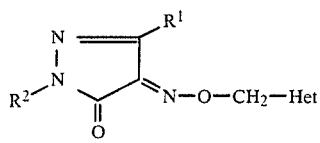

in which $R^1$ and $R^2$ independently of one another each represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case optionally substituted oxiranylalkyl, aralkyl, heterocyclyl or aryl and Het represents an optionally substituted heterocyclic radical, have been found.

The compounds of the formula (I) can exist as geometric isomers or isomer mixtures of different composition. Both the pure isomers and the isomer mixtures are claimed according to the invention.

It has furthermore been found that the new substituted pyrazolin-5-ones of the general formula (I)

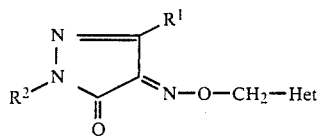

in which $R^1$ and $R^2$ independently of one another each represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case optionally substituted oxiranylalkyl, aralkyl, heterocyclyl or aryl and Het represents an optionally substituted heterocyclic radical, are obtained by a process in which (a) 4-oximino-pyrazolin-5-ones of the formula (II)

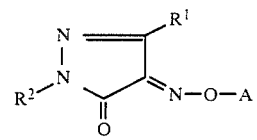

in which
$R^1$ and $R^2$ have the abovementioned meaning and
A represents hydrogen or an alkali metal cation,
are reacted with alkylating agents of the formula (III)

$$\text{Het—CH}_2\text{—X} \qquad (III)$$

in which
Het has the abovementioned meaning and
X represents an electron-withdrawing leaving group,
if appropriate in the presence of a diluent, if appropriate in the presence of an acid-binding agent and if appropriate in the presence of a catalyst, or in which (b) the alkoximinocarboxylic acid esters of the formula (IV)

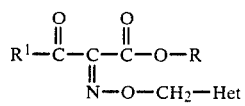

in which
R represents alkyl and
$R^1$ and Het have the abovementioned meaning,
are reacted with hydrazine derivatives of the formula (V)

$$R^2\text{—NH—NH}_2 \qquad (V)$$

in which
$R^2$ has the abovementioned meaning,
if appropriate in the presence of a diluent, or in which
(c) the 4-alkoximino-pyrazolin-5-ones obtainable by process (a) or by process (b), of the formula (Ia)

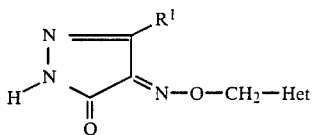

in which
$R^1$ and Het have the abovementioned meaning,
are reacted with alkylating agents of the formula (VI)

$$R^{2'}\text{—Y} \qquad (VI)$$

in which
$R^{2'}$ represents alkyl, alkenyl, alkinyl, cyanoalkyl, hydroxyalkyl, alkoxyalkyl, alkylthioalkyl, hydroxycarbonylalkyl or alkoxycarbonylalkyl, or represents in each case optionally substituted aralkyl or heterocyclyl and
Y represents an electron-withdrawing leaving group,
if appropriate in the presence of a diluent, if appropriate in the presence of an acid-binding agent and if appropriate in the presence of a catalyst.

Finally, it has been found that the new substituted pyrazolin-5-ones of the formula (I) have fungicidal and bactericidal properties.

Surprisingly, the new substituted pyrazolin-5-ones of the formula (I) exhibit better fungicidal properties than zinc ethylene-1,2-bis-dithiocarbamate, which is known from the prior art and is a closely related compound from the point of view of its action.

Formula (I) provides a general definition of the substituted pyrazolin-5-ones according to the invention. Preferred compounds of the formula (I) are those in which $R^1$ and $R^2$ independently of one another each represent hydrogen, or represent in each case straight-chain or branched alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl with in each case up to 8 carbon atoms in the individual alkyl, alkenyl or alkinyl parts, or represent oxiranylalkyl with 1 to 4 carbon atoms in the straight-chain or branched alkyl part, or represent 1,1-dioxotetrahydrothienyl, or represent straight-chain or branched aralkyl which has 1 to 4 carbon atoms in the alkyl part and 6 to 10 carbon atoms in the aryl part and is optionally monosubstituted or polysubstituted by identical or different substituents, or represent aryl which has 6 to 10 carbon atoms and is optionally monosubstituted or polysubstituted by identical or different substituents, possible substituents in the aryl part in each case being: halogen, cyano, nitro, hydroxyl, in each case straight-chain or branched alkyl, alkoxy, dioxyalkylene, alkylcarbonyloxy and alkylthio with in each case up to 4 carbon atoms, straight-chain or branched halogenoalkyl, halogenoalkoxy and halogenoalkylthio with in each case up to 4 carbon atoms and up to 9 identical or different halogen atoms and phenyl and Het represents a saturated or unsaturated five-membered or six-membered heterocyclic radical which has one to 3 heteroatoms, in particular nitrogen, oxygen and/or sulphur, and is optionally monosubstituted or polysubstituted by identical or different substituents and/or benzo-fused, possible substituents being: hydroxyl, halogen, cyano, nitro, in each case straight-chain or branched alkyl, alkoxy and halogenoalkyl with in each case 1 to 4 carbon atoms and, in the case of the halogenoalkyl 1 to 9 identical or different halogen atoms and phenyl which is optionally monosubstituted or polysubstituted by identical or different substituents from the group comprising lower alkyl, lower alkoxy, halogen and/or nitro.

Particularly preferred compounds of the formula (I) are those in which $R^1$ and $R^2$ independently of one another in each case represent hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represent 1,1-dioxotetrahydrothien-3-yl, or represent phenyl or benzyl which is optionally mono-, di- or trisubstituted by identical or different substituents, possible substituents being: fluorine, chlorine, bromine, iodine, cyano, nitro, hydroxyl, methyl, ethyl, n- or i-propyl, n-, i-, s- or t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl and Het represents a heterocyclic radical of the formula

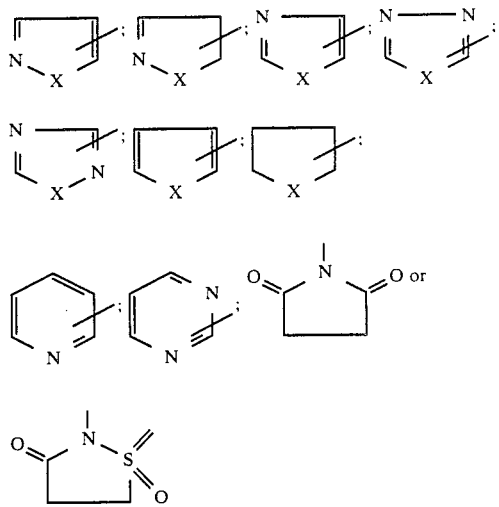

which is optionally mono-, di- or trisubstituted by identical or different substituents and/or benzo-fused, possible substituents in each case being: fluorine, chlorine, bromine, methyl, ethyl, n- or i-propyl, n-, i-, s- or t-butyl, methoxy, ethoxy, trifluoromethyl and phenyl which is optionally mono-, di- or trisubstituted by identical or different substituents from the group comprising chlorine, nitro, methyl and/or methoxy and wherein X in each case represents oxygen or sulphur.

The compounds listed by name in the preparation examples may be mentioned specifically.

If, for examle, 4-hydroximino-1,3-dimethyl-pyrazolin-5-one and 3-methyl-5-chloromethyl-1,2-oxazole are used as starting substances, the course of the reaction in process (a) according to the invention can be represented by the following equation:

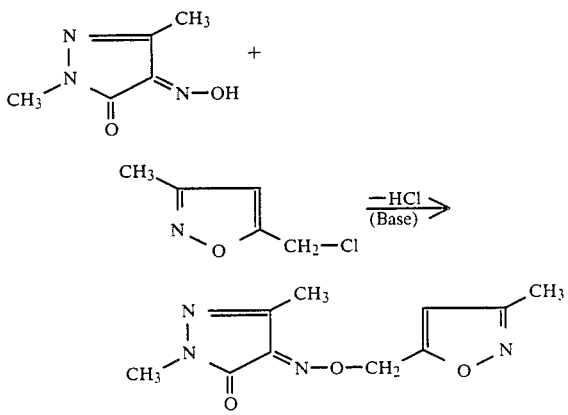

If, for example, ethyl β-keto-α-[(3-ethylisoxazol-5-yl)-methoximino]-butyrate and hydrazine hydrate are used as starting substances, the course of the reaction in process (b) according to the invention can be represented by the following equation:

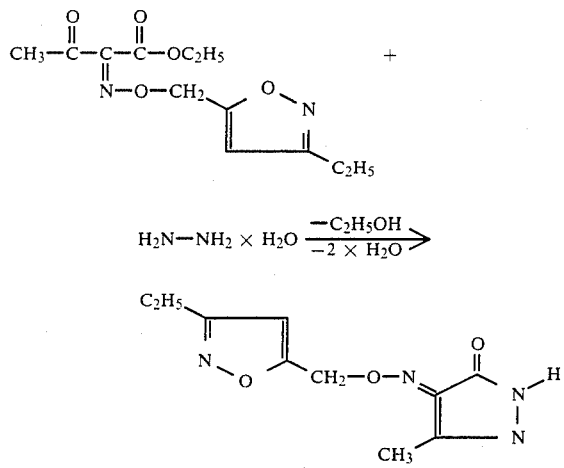

If, for example, 4-(benzoxazol-2-ylmethyl-oximino)-3-methyl-pyrazolin-5-one and chloroacetonitrile are used as starting substances, the course of the reaction in process (c) according to the invention can be represented by the following equation:

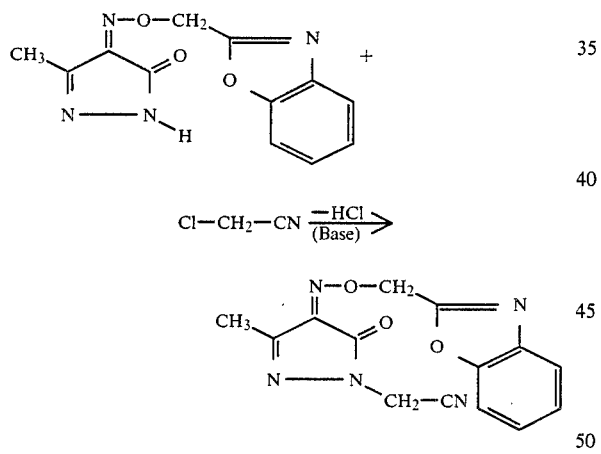

Formula (II) provides a general definition of the 4-oximino-pyrazolin-5-ones required as starting substances for carrying out process (a) according to the invention. In this formula (II), $R^1$ and $R^2$ preferably represent those radicals which have already been mentioned for this substituent in the description of the substances of the formula (I) according to the invention. A preferably represents hydrogen, or represents a sodium or potassium cation.

The 4-oximino-pyrazolin-5-ones of the formula (II) are known in some cases [compare, for example, Ber. dtsch. chem. Ges. 29, 249 (1896); Coll. Czech. Chem. Commun. 25, 55 (1960); Arch. Pharm. 309, 900 (1976); and Liebigs Ann. Chem. 1976, 1380].

They are obtained, for example, by a process in which β-keto esters of the formula (VII)

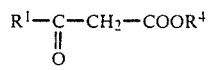

in which $R^1$ has the abovementioned meaning and
$R^4$ represents lower alkyl, in particular methyl or ethyl, or in which ethoxymethylenemalonates of the formula (VIII)

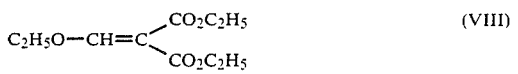

are initially hydrolyzed in a 1st stage with hydrazines of the formula (V)

$$R^2-NH-NH_2 \quad (V)$$

in which $R^2$ has the abovementioned meaning, if appropriate in the presence of a diluent, such as, for example, ethanol, at temperatures between 0° C. and 100° C., the 4-ethoxycarbonylpyrazolin-5-ones resulting from the malonate of the formula (VIII), of the formula (IX)

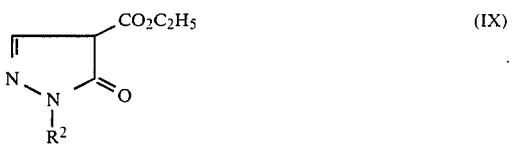

in which $R^2$ has the abovementioned meaning, are hydrolyzed and decarboxylated in an intermediate step by customary methods, for example with aqueous hydrochloric acid at temperatures between 50° C. and 120° C., and the pyrazolin-5-ones thus obtainable, of the formula (X)

in which $R^1$ and $R^2$ have the abovementioned meaning, are reacted in a 2nd stage (or 3rd stage) with a nitrosating agent, such as, for example, isopentyl nitrite or sodium nitrite, if appropriate in the presence of a diluent, such as, for example, ethanol, water or aqueous hydrochloric acid, and if appropriate in the presence of a base, such as, for example, sodium methylate, at temperatures between −20° C. and +50° C.

Formula (III) provides a general definition of the alkylating agents required as starting substances for carrying out process (a) according to the invention. In this formula (III), Het represents those radicals which have already been mentioned for these substituents in connection with the description of the substances of the formula (I) according to the invention. X preferably represents halogen, in particular chlorine, bromine or iodine, or represents optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy.

The alkylating agents of the formula (III) are generally known compounds of organic chemistry.

The β-keto esters of the formula (VII) and the ethoxymethylenemalonates of the formula (VIII) are likewise generally known.

Formula (IV) provides a general definition of the alkoximinocarboxylic acid esters required as starting substances for carrying out process (b) according to the invention. In this formula (IV), $R^1$ and Het represent those radicals which have already been mentioned for these substituents in connection with the description of the substances of the formula (I) according to the invention. R preferably represents straight-chain or branched alkyl with 1 to 4 carbon atoms, in particular methyl or ethyl.

The alkoximinocarboxylic acid esters of the formula (IV) are not yet known.

They are obtained by a process in which hydroximinocarboxylic acid esters of the formula (XI)

$$R^1-\underset{\underset{N-OH}{\parallel}}{C}-\underset{}{\overset{O}{\underset{\parallel}{C}}}-\overset{O}{\underset{\parallel}{C}}-OR \qquad (XI)$$

in which
   R and $R^1$ have the abovementioned meaning, are reacted with alkylating agents of the formula (III)

$$Het-CH_2-X \qquad (III)$$

in which
   Het has the abovementioned meaning and
   X represents an electron-withdrawing leaving group, in particular chlorine, bromine or iodine, or represents optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy,
if appropriate in the presence of a diluent, such as, for example, acetonitrile, and if appropriate in the presence of an acid-binding agent, such as, for example, triethylamine, at temperatures between $+10°$ C. and $+80°$ C.

The hydroximinocarboxylic acid esters of the formula (XI) are generally known compounds of organic chemistry (compare, for example, Helv. Chim. Acta 67, 906-915 [1984]; French Patent Application No. 2,434,572; Yakugaku Zasshi 87, 1209-1211 [1967] or Chem. Ber. 100, 1245-1247 [1967]).

Formula (Ia) provides a general definition of the 4-alkoximinopyrazolin-5-ones required as starting substances for carrying out process (c) according to the invention. In this formula (Ia), $R^1$ and Het preferably represent those radicals which have already been mentioned for these substituents in connection with the description of the substances of the formula (I) according to the invention.

The 4-alkoximinopyrazolin-5-ones of the formula (Ia) are compounds according to the invention and are obtainable with the aid of processes (a) or (b) according to the invention.

Formula (VI) provides a general definition of the alkylating agents furthermore required as starting substances for carrying out process (c) according to the invention. In this formula (VI), $R^{2'}$ preferably represents those radicals which have already been mentioned for the substituent $R^2$ in connection with the description of the substances of the formula (I) according to the invention, with the exception of the hydrogen radical and the optionally substituted aryl radicals. Y preferably represents those leaving groups which have already been mentioned for the substituent X in the description of the alkylating agents of the formula (III).

The alkylating agents of the formula (VI) are likewise generally known compounds of organic chemistry.

Possible diluents for carrying out process (a) according to the invention are inert organic solvents or aqueous systems.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride; ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate; sulphoxides, such as dimethylsulphoxide, or also water or aqueous-organic two-phase mixtures, such as methylene chloride/water or toluene/water.

If appropriate, process (a) according to the invention is carried out in the presence of an acid-binding agent. Possible acid-binding agents are all the customary inorganic or organic bases. These include, for example, alkali metal hydroxides, amides, alcoholates or hydrides, such as sodium hydroxide or potassium hydroxide, sodium methylate or potassium t-butylate, sodium hydride or sodium amide; alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperature can be varied within a substantial range in carrying out process (a) according to the invention. The reaction is in general carried out at temperatures between $-20°$ C. and $+200°$ C., preferably at temperatures between $0°$ C. and $+150°$ C.

In carrying out process (a) according to the invention, in general 1.0 to 3.0 moles, preferably 1.0 to 1.5 moles, of alkylating agent of the formula (III) and, if appropriate, 1.0 to 3.0 moles, preferably 1.0 to B 1.5 moles, of acid-binding agent are employed per mole of 4-oximino-pyrazolin-5-one of the formula (II).

If an organic-aqueous two-phase system is used, the reaction can be carried out, if appropriate, in the presence of 0.1 to 1 mole of a suitable phase transfer catalyst, such as, for example, a quaternary ammonium or phosphonium compound. Examples which may be mentioned are triethylbenzylammonium chloride and benzyl-dodecyldimethylammonium chloride.

The reaction products of the formula (I) are worked up and isolated by customary methods.

Possible diluents for carrying out process (b) according to the invention are likewise inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride; ethers, such as diethyl ether, dioxane, tetrahydrofuran or ethylene glycol dimethyl or diethyl ether, or alcohols, such as methanol, ethanol or propanol.

The reaction temperatures can be varied within a substantial range in carrying out process (b) according to the invention. The reaction is in general carried out at temperatures between 0° C. and 150° C., preferably at temperatures between 20° C. and 120° C.

For carrying out process (b) according to the invention, in general 0.8 to 2.5 moles, preferably 1.0 to 1.2 moles, of hydrazine derivative of the formula (V) are employed per mole of alkoximinocarboxylic acid ester of the formula (IV). The reaction is carried out and the reaction products of the formula (I) are worked up and isolated by customary methods.

Possible diluents for carrying out process (c) according to the invention are likewise inert organic solvents or aqueous systems. The organic solvents or aqueous-organic two-phase mixtures mentioned for process (a) are preferably used.

If appropriate, process (c) according to the invention is carried out in the presence of an acid-binding agent. Acid-binding agents which are preferably used are the inorganic or organic bases mentioned for process (a).

The reaction temperatures can likewise be varied within a substantial range in carrying out process (c) according to the invention. The reaction is in general carried out at temperatures between −20° C. and +200° C., preferably at temperatures between 0° C. and +150° C.

In carrying out process (c) according to the invention, in general 1.0 to 3.0 moles, preferably 1.0 to 1.5 moles, of alkylating agent of the formula (VI) and, if appropriate, 0.5 to 3.0 moles, preferably 0.6 to 1.5 moles, of acid-binding agent are employed per mole of 4-alkoximino-pyrazolin-5-one of the formula (Ia).

The reaction is carried out and the reaction products of the formula (I) are worked up and isolated as described for process (a) or by generally customary processes.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deteromycetes.

Bactericidal agents are used in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, Syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae*; and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds; and of the soil.

The active compounds according to the invention can be used here with particularly good success for combating cereal diseases caused, for example, by Cochliobolus sativus, Leptosphaeria nodorum, Erysiphe graminis or Pyrenophora teres, for combating vegetable diseases caused, for example, by the causative organism of brown rot of tomato (*Phytophthora infestans*), or for combating rice diseases, such as, for example, against the causative organism of rice spot disease (*Pyricularia oryzae*) or against the causative organism *Pellicularia sasakii*. The active compounds according to the invention thereby also show, in addition to a protective activity, systemic properties, and furthermore also a good activity against the bacterial disease *Erwinia amylovora* (fire blight). The fungicidal activity of the compounds according to the invention is also found in vitro in the agar plant test.

Besides an outstanding protective activity, the active compounds according to the invention also exhibit very good systemic properties. They are distinguished by a broad fungicidal in vitro action and by additional bactericidal properties.

The active compounds can be converted to the customary formulations, such as solutions, emulsions, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

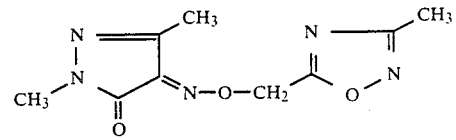

(Process a)

First 11.1 g (0.11 mole) of triethylamine and then, dropwise, 11.35 g (0.085 mole) of 3-methyl-5-chloromethyl-1,2,4-oxadiazole are added to 12 g (0.085 mole) of 1,3-dimethyl-4-hydroximino-pyrazolin-5-one in 100 ml of acetonitrile, while stirring. When the addition has ended, the mixture is warmed at 50° C. for one hour, the solvent is removed in vacuo, the residue is taken up in chloroform, the mixture is washed several times with water and dried over magnesium sulphate and the solvent is removed in vacuo. The oil which remains is purified by chromatography (silica gel/mobile phase: chloroform/ether 10:1) and the product is crystallized from petroleum ether.

9.9 g (49% of theory) of 4-[(3-methyl-1,2,4-oxadiazol-5-yl)-methoximino]-1,3-dimethyl-pyrazolin-5-one of melting point 54° C. are obtained.

Preparation of the starting compound

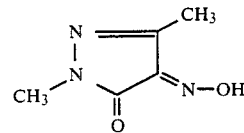

183 g (1.56 moles) of isopentyl nitrite are added dropwise to 175 g (1.56 moles) of 1,3-dimethyl-pyrazolin-5-one and 84.4 g (1.56 moles) of sodium methylate in 1 l of absolute ethanol, while stirring and cooling with ice, so that the internal temperature does not exceed 25° C. to 30° C. When the addition has ended, the mixture is stirred at room temperature for a further 24 hours and the sodium salt of 1,3-dimethyl-4-hydroximino-pyrazolin-5-one which has precipitated out is filtered off with suction. The crystalline product is dissolved in 1 l of water and acidified with glacial acetic acid. For complete precipitation, the mixture is cooled at 0° C. for several hours and the product is then filtered off with suction.

162 g (74% of theory) of 1,3-dimethyl-4-hydroximino-pyrazolin-5-one of melting point 93° C. are obtained.

EXAMPLE 2

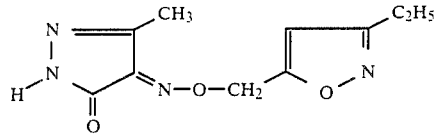

(Process b)

320 g (1.194 moles) of ethyl β-keto-α-[(3-ethylisoxazol-5-yl)-methoximino]-butyrate in 400 ml of ethanol are warmed to 70° C. dropwise with 59.5 g (1.19 moles) of hydrazine hydrate at room temperature, while stirring. When the addition has ended, stirring is continued at the reflux temperature for a further 3 hours and the solvent is then distilled off from the cooled reaction mixture under reduced pressure. The residue, which crystallizes when stirred with ethanol/diethyl ether, is filtered off with suction and dried.

205 g (73% of theory) of 4-[(3-ethylisoxazol-5-yl)-methoximino]-3-methyl-pyrazolin-5-one of melting point 118° C. are obtained.

EXAMPLE 3

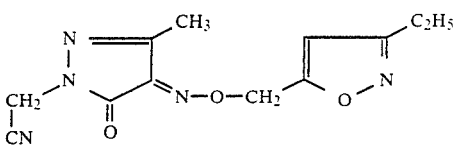

(Process c)

205 g (0.869 mole) of 4-[3-ethylisoxazol-5-yl)-methoximino]-3-methyl-pyrazolin-5-one, 82.8 g (0.6 mole) of powdered potassium carbonate and 63.4 ml (1 mole) of chloroacetonitrile in 1,000 ml of acetone are heated under reflux for 4 hours. Thereafter, a further 21.1 ml (0.33 mole) of chloroacetonitrile are added and the mixture is heated under reflux for a further 2 hours. The cooled reaction mixture is concentrated in vacuo, the residue is taken up in methylene chloride, the insoluble constituents are filtered off, the filtrate is washed several times, dried over sodium sulphate and concentrated in vacuo and the residue is purified by chromatography (silica gel).

74.3 g (35% of theory) of 1-cyanomethyl-4-[(3-ethylisoxazol-5-yl)-methoximino]-3-methyl-pyrazolin-5-one are obtained as an oil.

$^1$H-NMR (CDCl$_3$/tetramethylsilane as the internal standard): δ=5.5 ppm (=N—O—CH$_2$—).

The following substituted pyrazolin-5-ones of the general formula (I) are obtained in a corresponding manner and in accordance with the general statements on the preparation:

TABLE 1

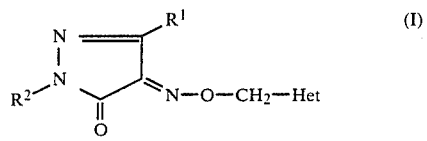

| Example No. | R$^1$ | R$^2$ | Het | Physical data |
|---|---|---|---|---|
| 4 | H | CH$_3$ | (5-methylisoxazol-3-yl)CH$_2$ | Melting point 146–148° C. |
| 5 | CH$_3$ | H | (5-methylisoxazol-3-yl)CH$_2$ | Melting point 135° C. |
| 6 | CH$_3$ | CH$_3$ | (5-methylisoxazol-3-yl)CH$_2$ | Melting point 101° C. |
| 7 | CH$_3$ | (CH$_3$)$_3$C— | (5-methylisoxazol-3-yl)CH$_2$ | $^1$H—NMR* 5.41 ppm |
| 8 | CH$_3$ | CH$_2$=CH—CH$_2$— | (5-methylisoxazol-3-yl)CH$_2$ | $^1$H—NMR* 5.45 ppm |

TABLE 1-continued (structure I): pyrazole with R¹ at position 4, R² on N, =N—O—CH₂—Het substituent, and C=O

| Example No. | R¹ | R² | Het | Physical data |
|---|---|---|---|---|
| 9 | CH₃ | NC—CH₂— | 3,5-dimethylisoxazol-4-yl | ¹H—NMR* 5.5 ppm |
| 10 | CH₃ | HO—CH₂—CH₂— | 3,5-dimethylisoxazol-4-yl | ¹H—NMR* 5.5 ppm |
| 11 | CH₃ | CH₃O—CO—CH₂— | 3,5-dimethylisoxazol-4-yl | ¹H—NMR* 5.6 ppm |
| 12 | CH₃ | phenyl | 3,5-dimethylisoxazol-4-yl | ¹H—NMR* 5.0 ppm |
| 13 | CH₃ | 2-chlorophenyl | 3,5-dimethylisoxazol-4-yl | ¹H—NMR* 5.5 ppm |
| 14 | CH₃ | 4-nitrophenyl | 3,5-dimethylisoxazol-4-yl | Melting point 180° C. (decomposition) |
| 15 | CH₃ | 4-methylphenyl | 3,5-dimethylisoxazol-4-yl | Melting point 104° C. |
| 16 | C₂H₅ | CH₃ | 3,5-dimethylisoxazol-4-yl | ¹H—NMR* 5.5 ppm |
| 17 | CH₃—(CH₂)₂— | CH₃ | 3,5-dimethylisoxazol-4-yl | ¹H—NMR* 5.46 ppm |
| 18 | (CH₃)₃C— | CH₃ | 3,5-dimethylisoxazol-4-yl | Melting point 73° C. |
| 19 | C₂H₅—O—CO— | CH₃ | 3,5-dimethylisoxazol-4-yl | Melting point 100° C. |
| 20 | phenyl | CH₃ | 3,5-dimethylisoxazol-4-yl | Melting point 83° C. |

TABLE 1-continued $$\text{(I)}$$

Structure (I): pyrazole ring with substituents $R^1$ on C=N carbon, $R^2$ on N, and =N—O—CH$_2$—Het on the adjacent carbon, with C=O.

| Example No. | $R^1$ | $R^2$ | Het | Physical data |
|---|---|---|---|---|
| 21 | CH$_3$ | CH$_3$ | isoxazole with C$_2$H$_5$ and CH$_3$ | $^1$H—NMR* 5.5 ppm |
| 22 | CH$_3$ | (CH$_3$)$_3$C— | isoxazole with C$_2$H$_5$ and CH$_3$ | $^1$H—NMR* 5.4 ppm |
| 23 | CH$_3$ | HO—CH$_2$—CH$_2$— | isoxazole with C$_2$H$_5$ and CH$_3$ | $^1$H—NMR* 5.5 ppm |
| 24 | CH$_3$ | phenyl | isoxazole with C$_2$H$_5$ and CH$_3$ | $^1$H—NMR* 5.0 ppm |
| 25 | CH$_3$ | 2-chlorophenyl | isoxazole with C$_2$H$_5$ and CH$_3$ | $^1$H—NMR* 5.52 ppm |
| 26 | CH$_3$ | 4-methylphenyl | isoxazole with C$_2$H$_5$ and CH$_3$ | Melting point 103° C. |
| 27 | C$_2$H$_5$ | CH$_3$ | isoxazole with C$_2$H$_5$ and CH$_3$ | $^1$H—NMR* 5.58 ppm |
| 28 | CH$_3$—(CH$_2$)$_2$— | CH$_3$ | isoxazole with C$_2$H$_5$ and CH$_3$ | $^1$H—NMR* 5.46 ppm |
| 29 | (CH$_3$)$_3$C— | CH$_3$ | isoxazole with C$_2$H$_5$ and CH$_3$ | Melting point 61° C. |
| 30 | C$_2$H$_5$—O—C(=O)— | CH$_3$ | isoxazole with C$_2$H$_5$ and CH$_3$ | Melting point 88° C. |
| 31 | phenyl | CH$_3$ | isoxazole with C$_2$H$_5$ and CH$_3$ | Melting point 78° C. |
| 32 | H | CH$_3$ | isoxazole with C(CH$_3$)$_3$ and CH$_3$ | $^1$H—NMR* 5.45 ppm |

TABLE 1-continued $$\text{(I)}$$

Structure: pyrazolone with R¹ on the C=CH-N, R² on N, and =N-O-CH₂-Het substituent

| Example No. | R¹ | R² | Het | Physical data |
|---|---|---|---|---|
| 33 | CH₃ | CH₃ | 3-C(CH₃)₃-5-methylisoxazole | ¹H—NMR* 5.5 ppm |
| 34 | CH₃ | NC—CH₂—CH₂— | 3-C(CH₃)₃-5-methylisoxazole | ¹H—NMR* 5.5 ppm |
| 35 | CH₃ | HO—CH₂—CH₂— | 3-C(CH₃)₃-5-methylisoxazole | ¹H—NMR* 5.5 ppm |
| 36 | H | H | 3-(4-Cl-phenyl)-5-methylisoxazole | Melting point 124–126 |
| 37 | H | CH₃ | 3-(4-Cl-phenyl)-5-methylisoxazole | ¹H—NMR* 5.5 ppm |
| 38 | CH₃ | H | 3-(4-Cl-phenyl)-5-methylisoxazole | Melting point 163° C. |
| 39 | CH₃ | CH₃ | 3-(4-Cl-phenyl)-5-methylisoxazole | ¹H—NMR* 5.5 ppm |
| 40 | CH₃ | NC—CH₂— | 3-(4-Cl-phenyl)-5-methylisoxazole | ¹H—NMR* 5.56 ppm |
| 41 | CH₃ | NC—CH₂—CH₂— | 3-(4-Cl-phenyl)-5-methylisoxazole | ¹H—NMR* 5.5 ppm |

TABLE 1-continued

Structure (I): pyrazolinone with R¹ on C=, R²–N, and =N–O–CH₂–Het substituent

| Example No. | R¹ | R² | Het | Physical data |
|---|---|---|---|---|
| 42 | CH₃ | C₂H₅O−C(=O)−CH₂− | 3-(4-chlorophenyl)-5-methylisoxazol-4-yl | Melting point 108° C. |
| 43 | C₂H₅ | CH₃ | 3-(4-chlorophenyl)-5-methylisoxazol-4-yl | ¹H—NMR* 5.5 ppm |
| 44 | CH₃O—CH₂— | NC—CH₂—CH₂— | 3-(4-chlorophenyl)-5-methylisoxazol-4-yl | ¹H—NMR* 5.6 ppm |
| 45 | CH₃O−C(=O)−CH₂− | CH₃ | 3-(4-chlorophenyl)-5-methylisoxazol-4-yl | ¹H—NMR* 5.53 ppm |
| 46 | CH₃ | CH₃ | 3-phenyl-5-methyl-4,5-dihydroisoxazol-5-yl | ¹H—NMR* 5.28 ppm |
| 47 | CH₃ | CH₃ | 3-(4-chlorophenyl)-5-methyl-4,5-dihydroisoxazol-5-yl | Melting point 135–140° C. |
| 48 | C₂H₅ | CH₃ | 3-(4-chlorophenyl)-5-methyl-4,5-dihydroisoxazol-5-yl | Melting point 133–140° C. |
| 49 | CH₃O—CH₂— | CH₃ | 3-(4-chlorophenyl)-5-methyl-4,5-dihydroisoxazol-5-yl | ¹H—NMR* 4.6 ppm |

TABLE 1-continued $$\text{(I)}$$

Structure: Pyrazolone with R¹ at position 4, R² on N, and =N—O—CH₂—Het oxime substituent.

| Example No. | R¹ | R² | Het | Physical data |
|---|---|---|---|---|
| 50 | CH₃O—C(=O)—CH₂— | CH₃ | 3-(4-chlorophenyl)-5-methyl-4,5-dihydroisoxazol-5-yl | ¹H—NMR* 5.52 ppm |
| 51 | H | HO—CH₂—CH₂— | 2-methyl-5-phenyl-1,3,4-oxadiazol-yl | Melting point 118–119° C. |
| 52 | CH₃ | CH₃ | 2-methyl-5-phenyl-1,3,4-oxadiazol-yl | ¹H—NMR* 5.66 ppm |
| 53 | CH₃ | NC—CH₂—CH₂— | 2-methyl-5-phenyl-1,3,4-oxadiazol-yl | ¹H—NMR* 5.66 ppm |
| 54 | C₂H₅ | CH₃ | 2-methyl-5-phenyl-1,3,4-oxadiazol-yl | Melting point 82° C. |
| 55 | CH₃O—CH₂— | CH₃ | 2-methyl-5-phenyl-1,3,4-oxadiazol-yl | ¹H—NMR* 5.66 ppm |
| 56 | CH₃O—CH₂— | NC—CH₂—CH₂— | 2-methyl-5-phenyl-1,3,4-oxadiazol-yl | Melting point 106° C. |
| 57 | CH₃ | (CH₃)₃C— | 3,5-dimethyl-1,2,4-oxadiazol-yl | ¹H—NMR* 5.58 ppm |
| 58 | CH₃ | phenyl | 3,5-dimethyl-1,2,4-oxadiazol-yl | Melting point 98° C. |

TABLE 1-continued $$\text{(I)}$$

Structure (I): pyrazolone with R¹ on C=N-N, R²-N on ring nitrogen, and =N-O-CH₂-Het substituent, with ring C=O.

| Example No. | R¹ | R² | Het | Physical data |
|---|---|---|---|---|
| 59 | CH₃ | 2-Cl-C₆H₄- | 3-methyl-5-methyl-isoxazol-4-yl (N=C(CH₃)-C(CH₃)=N-O) | ¹H—NMR* 5.66 ppm |
| 60 | CH₃ | 4-CH₃-C₆H₄- | 3-methyl-5-methyl-isoxazol-4-yl | Melting point 98° C. |
| 61 | CH₃ | 4-O₂N-C₆H₄- | 3-methyl-5-methyl-isoxazol-4-yl | Melting point 160° C. |
| 62 | C₂H₅ | CH₃ | 3-methyl-5-methyl-isoxazol-4-yl | ¹H—NMR* 5.6 ppm |
| 63 | C₆H₅ | CH₃ | 3-methyl-5-methyl-isoxazol-4-yl | Melting point 75° C. |
| 64 | CH₃—(CH₂)₂— | CH₃ | 3-methyl-isoxazol-4-yl | ¹H—NMR* 5.6 ppm |
| 65 | (CH₃)₃C— | CH₃ | 3-methyl-isoxazol-4-yl | ¹H—NMR* 5.58 ppm |
| 66 | H | CH₃ | benzisoxazol-3-yl | ¹H—NMR* 5.83 ppm |
| 67 | H | NC—CH₂—CH₂— | benzisoxazol-3-yl | ¹H—NMR* 5.83 ppm |
| 68 | H | HO—CH₂—CH₂— | benzisoxazol-3-yl | ¹H—NMR* 5.83 ppm |
| 69 | CH₃ | H | benzisoxazol-3-yl | Melting point 102° C. |
| 70 | CH₃ | CH₃ | benzisoxazol-3-yl | ¹H—NMR* 5.83 ppm |

TABLE 1-continued $$\text{(I)}$$

Structure: pyrazole ring with R¹ at position, N—N-R², C=O, and C=N—O—CH₂—Het substituent

| Example No. | R¹ | R² | Het | Physical data |
|---|---|---|---|---|
| 71 | CH₃ | NC—CH₂—CH₂— | 3-methylbenzisoxazol-ylidene | ¹H—NMR* 5.83 ppm |
| 72 | CH₃ | HO—CH₂—CH₂— | 3-methylbenzisoxazol-ylidene | Melting point 114–116° C. |
| 73 | CH₃O—CH₂— | NC—CH₂—CH₂— | 3-methylbenzisoxazol-ylidene | ¹H—NMR* 5.91 ppm |
| 74 | H | H | benzoxazol-2-yl (methyl) | Melting point 134° C. |
| 75 | H | CH₃ | benzoxazol-2-yl (methyl) | ¹H—NMR* 5.66 ppm |
| 76 | CH₃ | H | benzoxazol-2-yl (methyl) | Melting point 130–132° C. |
| 77 | CH₃ | CH₃ | benzoxazol-2-yl (methyl) | Melting point 110–114° C. |
| 78 | CH₃ | NC—CH₂— | benzoxazol-2-yl (methyl) | ¹H—NMR* 5.66 ppm |
| 79 | CH₃ | NC—CH₂—CH₂— | benzoxazol-2-yl (methyl) | ¹H—NMR* 5.66 ppm |
| 80 | CH₃ | HO—CH₂—CH₂ | benzoxazol-2-yl (methyl) | ¹H—NMR* 5.66 ppm |
| 81 | H | H | 5-chlorobenzoxazol-2-yl (methyl) | Melting point 112–115° C. |

TABLE 1-continued $$\text{(I)}$$

Structure: pyrazole with R¹ at 4-position, R² on N, and =N—O—CH₂—Het group

| Example No. | R¹ | R² | Het | Physical data |
|---|---|---|---|---|
| 82 | H | CH₃ | 2-methyl-benzoxazole with 5-Cl | Melting point 115° C. |
| 83 | CH₃ | H | 2-methyl-benzoxazole with 5-Cl | Melting point 160° C. |
| 84 | CH₃ | CH₃ | 2-methyl-benzoxazole with 5-Cl | ¹H—NMR* 5.66 ppm |
| 85 | CH₃ | NC—CH₂— | 2-methyl-benzoxazole with 5-Cl | ¹H—NMR* 5.7 ppm |
| 86 | CH₃ | NC—CH₂—CH₂— | 2-methyl-benzoxazole with 5-Cl | ¹H—NMR* 5.66 ppm |
| 87 | CH₃ | HO—CH₂—CH₂— | 2-methyl-benzoxazole with 5-Cl | Melting point 146–147° C. |
| 88 | CH₃ | H | 2,4-dimethyl-thiazole | Melting point 104° C. |
| 89 | CH₃ | CH₃ | 2,4-dimethyl-thiazole | ¹H—NMR* 5.5 ppm |
| 90 | CH₃ | (CH₃)₃C— | 2,4-dimethyl-thiazole | ¹H—NMR* 5.5 ppm |
| 91 | CH₃ | NC—CH₂— | 2,4-dimethyl-thiazole | Melting point 81° C. |
| 92 | CH₃ | NC—CH₂—CH₂— | 2,4-dimethyl-thiazole | Melting point 82° C. |
| 93 | CH₃ | HO—CH₂—CH₂— | 2,4-dimethyl-thiazole | ¹H—NMR* 5.5 ppm |

TABLE 1-continued $$\text{(I)}$$

Structure: pyrazole with R¹ at 4-position, R² on N, and =N—O—CH₂—Het substituent

| Example No. | R¹ | R² | Het | Physical data |
|---|---|---|---|---|
| 94 | CH₃ | 4-CH₃-C₆H₄- | 2-methylthiazol-4-yl | ¹H—NMR* 5.5 ppm |
| 95 | C₂H₅ | CH₃ | 2-methylthiazol-4-yl | ¹H—NMR* 5.53 ppm |
| 96 | CH₃O—CH₂— | CH₃ | 2-methylthiazol-4-yl | ¹H—NMR* 5.53 ppm |
| 97 | CH₃O—CH₂— | NC—CH₂—CH₂— | 2-methylthiazol-4-yl | ¹H—NMR* 5.53 ppm |
| 98 | C₂H₅O—C(O)— | CH₃ | 2-methylthiazol-4-yl | Melting point 119° C. |
| 99 | H | NC—CH₂—CH₂— | 2-phenylthiazol-4-yl | Melting point 116° C. |
| 100 | CH₃ | H | 2-phenylthiazol-4-yl | ¹H—NMR* 5.63 ppm |
| 101 | CH₃ | CH₃ | 2-phenylthiazol-4-yl | Melting point 91° C. |
| 102 | CH₃ | NC—CH₂— | 2-phenylthiazol-4-yl | Melting point 130° C. |
| 103 | CH₃ | NC—CH₂—CH₂— | 2-phenylthiazol-4-yl | Melting point 97° C. |
| 104 | CH₃ | HO—CH₂—CH₂— | 2-phenylthiazol-4-yl | Melting point 94° C. |

TABLE 1-continued $$\underset{R^2}{\overset{N}{\underset{|}{N}}}\underset{\underset{O}{\|}}{\overset{R^1}{\rightleftharpoons}}\underset{N-O-CH_2-Het}{}$$  (I)

| Example No. | R¹ | R² | Het | Physical data |
|---|---|---|---|---|
| 105 | CH₃ | 4-CH₃-C₆H₄- | 2-(phenyl)thiazol-5-yl | ¹H—NMR* 5.65 ppm |
| 106 | CH₃ | glycidyl (oxiranyl-CH₂-) | 2-(phenyl)thiazol-5-yl | ¹H—NMR* 5.6 ppm |
| 107 | CH₃O—CH₂— | CH₃ | 2-(phenyl)thiazol-5-yl | ¹H—NMR* 5.66 ppm |
| 108 | CH₃O—CH₂— | NC—CH₂—CH₂— | 2-(phenyl)thiazol-5-yl | ¹H—NMR* 5.66 ppm |
| 109 | C₂H₅—O—C(=O)— | CH₃ | 2-(phenyl)thiazol-5-yl | Melting point 95° C. |
| 110 | H | CH₃ | 2,4-dichlorothiazol-5-yl | ¹H—NMR* 5.5 ppm |
| 111 | CH₃ | H | 2,4-dichlorothiazol-5-yl | Melting point 154–156° C. |
| 112 | CH₃ | CH₃ | 2,4-dichlorothiazol-5-yl | Melting point 108–110° C. |
| 113 | CH₃ | NC—CH₂—CH₂— | 2,4-dichlorothiazol-5-yl | ¹H—NMR* 5.5 ppm |
| 114 | CH₃ | HO—CH₂—CH₂— | 2,4-dichlorothiazol-5-yl | Melting point 91° C. |
| 115 | H | CH₃ | 5-chlorothien-2-yl | ¹H—NMR* 5.5 ppm |

TABLE 1-continued

Structure (I):
$$\text{R}^2-\text{N(N=)}... \text{with R}^1, =\text{N}-\text{O}-\text{CH}_2-\text{Het}, \text{C=O}$$

| Example No. | R¹ | R² | Het | Physical data |
|---|---|---|---|---|
| 116 | CH₃ | H | 5-methyl-2-chlorothiophene | Melting point 116° C. |
| 117 | CH₃ | CH₃ | 5-methyl-2-chlorothiophene | ¹H—NMR* 5.5 ppm |
| 118 | CH₃ | NC—CH₂—CH₂— | 5-methyl-2-chlorothiophene | ¹H—NMR* 5.5 ppm |
| 119 | CH₃ | HO—CH₂—CH₂— | 5-methyl-2-chlorothiophene | ¹H—NMR* 5.5 ppm |
| 120 | H | H | 3-methyl-2-chlorothiophene | Melting point 80° C. |
| 121 | H | CH₃ | 3-methyl-2-chlorothiophene | ¹H—NMR* 5.43 ppm |
| 122 | H | NC—CH₂—CH₂— | 3-methyl-2-chlorothiophene | ¹H—NMR* 5.5 ppm |
| 123 | CH₃ | H | 3-methyl-2-chlorothiophene | Melting point 120° C. |
| 124 | CH₃ | CH₃ | 3-methyl-2-chlorothiophene | Melting point 64–66° C. |
| 125 | CH₃ | NC—CH₂— | 3-methyl-2-chlorothiophene | ¹H—NMR* 5.5 ppm |
| 126 | CH₃ | NC—CH₂—CH₂— | 3-methyl-2-chlorothiophene | ¹H—NMR* 5.43 ppm |
| 127 | CH₃ | HO—CH₂—CH₂— | 3-methyl-2-chlorothiophene | Melting point 94–96° C. |
| 128 | H | CH₃ | 3-methyl-2,5-dichlorothiophene | ¹H—NMR* 5.5 ppm |

TABLE 1-continued $$\text{(I)}$$

Structure: pyrazole ring with R¹ on C=N, R² on N, =N—O—CH₂—Het, and C=O

| Example No. | R¹ | R² | Het | Physical data |
|---|---|---|---|---|
| 129 | CH₃ | H | 3-methyl-2,5-dichlorothiophene | Melting point 120–122° C. |
| 130 | CH₃ | CH₃ | 3-methyl-2,5-dichlorothiophene | Melting point 65° C. |
| 131 | CH₃ | NC—CH₂— | 3-methyl-2,5-dichlorothiophene | ¹H—NMR* 5.5 ppm |
| 132 | CH₃ | CH₃ | tetrahydrofuran-2-yl | ¹H—NMR* 4.55 ppm |
| 133 | CH₃ | H | 2-methylpyridine | Melting point >150° C. (decomposition) |
| 134 | CH₃ | CH₃ | 2-methylpyridine | Melting point 80–82° C. |
| 135 | CH₃ | CH₃O—CO—CH₂— | 2-methylpyridine | ¹H—NMR* 5.6 ppm |
| 136 | CH₃ | CH₃O—CO—CH₂— | 3-methylpyridine | ¹H—NMR* 5.6 ppm |
| 137 | CH₃ | CH₃ | 2-methylquinoline | ¹H—NMR* 5.8 ppm |
| 138 | CH₃ | CH₃ | 4,6-dihydroxy-2-methylpyrimidine | Melting point >150° C. (decomposition) |
| 139 | CH₃ | H | N-methylphthalimide | Melting point 160–165° C. |

TABLE 1-continued

Structure (I):

$R^2$-N-N=C(R^1)-C(=N-O-CH_2-Het)-C(=O)- (pyrazolone ring)

| Example No. | $R^1$ | $R^2$ | Het | Physical data |
|---|---|---|---|---|
| 140 | $CH_3$ | $CH_3$ | N-methylphthalimide | Melting point 168° C. |
| 141 | $CH_3$ | $NC-CH_2-CH_2-$ | N-methylphthalimide | Melting point 150° C. |
| 142 | $CH_3$ | 4-methylphenyl | N-methylphthalimide | Melting point 140–145° C. |
| 143 | $CH_3$ | 3-methyl-sulfolanyl ($SO_2$) | N-methylphthalimide | Melting point 182° C. |
| 144 | $C_2H_5$ | $CH_3$ | N-methylphthalimide | Melting point 177° C. |
| 145 | $CH_3O-CH_2-$ | $CH_3$ | N-methylphthalimide | Melting point 165–175° C. |
| 146 | $C_2H_5O-CH_2$ | $CH_3$ | N-methylphthalimide | Melting point 138–145° C. |
| 147 | $CH_3S-CH_2-$ | $CH_3$ | N-methylphthalimide | $^1H$—NMR* 5.95 ppm |
| 148 | $CH_3O-C(=O)-CH_2-$ | $CH_3$ | N-methylphthalimide | Melting point 111° C. |

TABLE 1-continued $$\text{(I)}$$

Structure: pyrazolone with R¹ on C=N, R²-N on ring N, =N-O-CH₂-Het substituent, C=O on ring.

| Example No. | R¹ | R² | Het | Physical data |
|---|---|---|---|---|
| 149 | H | H | (N-methyl benzisothiazolinone 1,1-dioxide) | Melting point 184–186° C. |
| 150 | H | CH₃ | (N-methyl benzisothiazolinone 1,1-dioxide) | Melting point 90° C. |
| 151 | H | NC—CH₂—CH₂— | (N-methyl benzisothiazolinone 1,1-dioxide) | Melting point 172–176° C. |
| 152 | CH₃ | H | (N-methyl benzisothiazolinone 1,1-dioxide) | Melting point 206° C. |
| 153 | CH₃ | CH₃ | (N-methyl benzisothiazolinone 1,1-dioxide) | Melting point 177–179° C. |
| 154 | CH₃ | (CH₃)₃C— | (N-methyl benzisothiazolinone 1,1-dioxide) | $^1$H—NMR* 6.0 ppm |
| 155 | CH₃ | NC—CH₂—CH₂— | (N-methyl benzisothiazolinone 1,1-dioxide) | Melting point 176° C. |
| 156 | CH₃ | HO—CH₂—CH₂— | (N-methyl benzisothiazolinone 1,1-dioxide) | $^1$H—NMR* 6.0 ppm |
| 157 | CH₃ | C₆H₅— | (N-methyl benzisothiazolinone 1,1-dioxide) | $^1$H—NMR* 6.05 ppm |

TABLE 1-continued
(I)
| Example No. | R¹ | R² | Het | Physical data |
|---|---|---|---|---|
| 158 | $CH_3$ | 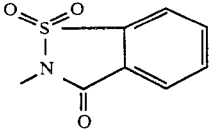 | 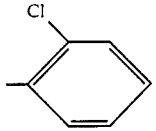 | Melting point 210° C. |
| 159 | $CH_3$ | 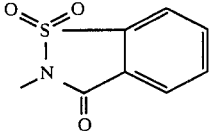 | 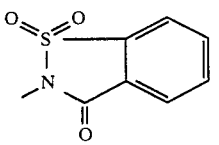 | Melting point 148° C. |
| 160 | $C_2H_5$ | H | 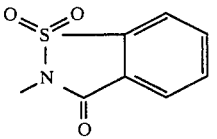 | Melting point 173° C. |
| 161 | $C_2H_5$ | $CH_3$ | 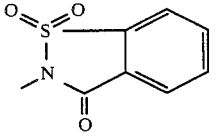 | Melting point 142–144° C. |
| 162 | $CH_3-(CH_2)_2-$ | H | 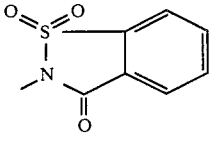 | Melting point 100° C. |
| 163 | $CH_3-(CH_2)_3-$ | H | 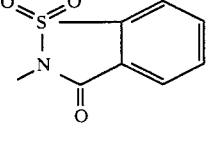 | Melting point 110° C. |
| 164 | $CH_3-(CH_2)_3-$ | $CH_3$ | 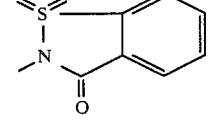 | Melting point 105° C. |
| 165 | $(CH_3)_3C-$ | $CH_3$ | 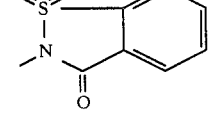 | Melting point 190° C. |
| 166 | $CH_3O-CH_2-$ | $CH_3$ | 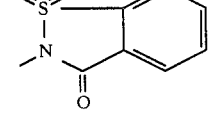 | Melting point 128° C. |

TABLE 1-continued $$\text{(I)}$$

Structure: pyrazole with R¹ at 4-position, R²–N at 1-position, =O at 5-position, and =N–O–CH₂–Het group

| Example No. | R¹ | R² | Het | Physical data |
|---|---|---|---|---|
| 167 | CH₃O—CH₂— | NC—CH₂—CH₂— | N-methyl-saccharin (1,2-benzisothiazol-3(2H)-one 1,1-dioxide) | ¹H—NMR* 6.12 ppm |
| 168 | C₂H₅—O—CO— | CH₃ | N-methyl-saccharin | ¹H—NMR* 6.06 ppm |
| 169 | C₆H₅— (phenyl) | CH₃ | N-methyl-saccharin | Melting point 196–198° C. |
| 170 | CH₃ | oxiranyl-CH₂— | 3-methyl-2,5-dichlorothiophene | ¹H—NMR* 5.4 ppm |
| 171 | CH₃ | CH₂=CH—CH₂— | 3-methyl-2,5-dichlorothiophene | ¹H—NMR* 5.35 ppm |
| 172 | CH₃ | HC≡C—CH₂— | 3-methyl-2,5-dichlorothiophene | ¹H—NMR* 5.4 ppm |
| 173 | CH₃ | C₂H₅O—CO—CH₂— | 3-methyl-2,5-dichlorothiophene | ¹H—NMR* 5.4 ppm |
| 174 | CH₃ | H₂N—CO—CH₂— | 3-methyl-2,5-dichlorothiophene | Melting point 162° C. |
| 175 | CH₃ | (CH₃)₂N—CO—CH₂— | 3-methyl-2,5-dichlorothiophene | ¹H—NMR* 5.3 ppm |
| 176 | CH₃ | C₂H₅NH—CO—CH₂— | 3-methyl-2,5-dichlorothiophene | Melting point 149° C. |
| 177 | CH₃ | CH₃—NH—CO—CH₂— | 3-methyl-2,5-dichlorothiophene | ¹H—NMR* 5.4 ppm |

TABLE 1-continued $$\begin{array}{c} R^1 \\ | \\ R^2-N-N=\text{(ring)}=N-O-CH_2-\text{Het} \\ \| \\ O \end{array} \quad (I)$$

| Example No. | $R^1$ | $R^2$ | Het | Physical data |
|---|---|---|---|---|
| 178 | $CH_3$ | $CH_3OCO-CH_2-$ | [3-methyl-2,5-dichlorothiophene] | $^1H-NMR^*$ 5.3 ppm |
| 179 | $CH_3$ | $-C_6H_4-NO_2$ | [2-(N-methylsulfonyl)benzamide] | $^1H-NMR^*$ 5.45 ppm |
| 180 | $CH_3$ | $-CH_2OH$ | [3-methyl-2,5-dichlorothiophene] | $^1H-NMR^*$ 5.3 ppm |
| 181 | H | $-CH_2COCH_3$ | [5-chlorobenzoxazole] | Melting Point 114° C. |
| 182 | H | $-CH_2CH_2OH$ | [3-methyl-2-chlorothiophene] | $^1H-NMR^*$ 5.5 ppm |

*The $^1H-NMR$ spectra were recorded in $CDCl_3$ with tetramethylsilane as the internal standard. As a rule the chemical shifts are stated as δ values for the grouping

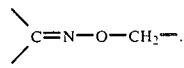

PREPARATION OF THE PRECURSORS OF THE FORMULA (IV)

EXAMPLE IV-1

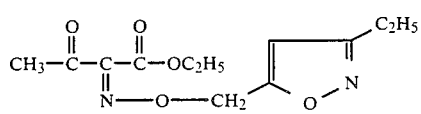

140 ml (1 mole) of triethylamine are added dropwise to 146 g (1 mole) of ethyl 2-hydroximino-3-oxo-butyrate [compare, for example, Helv. Chem. Acta. 67, 906–915 (1984)] and 159 g (1 mole) of 3-ethyl-5-chloromethylisoxazole in 600 ml of acetonitrile at room temperature, while stirring, and, when the addition has ended, the mixture is stirred at 50° C. for a further 6 hours. For working up, the triethylamine hydrochloride which has precipitated out is filtered off and the solvent is then removed in vacuo. The residue is taken up in methylene chloride, the mixture is washed several times with water, dried over sodium sulphate and concentrated in vacuo and the residue is distilled under a high vacuum.

157 g (59% of theory) of ethyl β-keto-α-[(3-ethylisoxazol-5-yl)-methoximino]-butyrate of boiling point 80° to 160° C./1.5 mbar are obtained.

The following alkoximinocarboxylic acid esters of the general formula (IV) are obtained in a corresponding manner and in accordance with the general statements on the preparation:

TABLE 2

$$\begin{array}{c} O \quad O \\ \| \quad \| \\ R^1-C-C-C-O-R \\ \| \\ N-O-CH_2-\text{Het} \end{array} \quad (IV)$$

| Example No. | $R^1$ | $R^2$ | Het | Physical data |
|---|---|---|---|---|
| IV-2 | $CH_3$ | $C_2H_5$ | [3,5-dimethylisoxazole] | $^1H-NMR^*$ 5.33 ppm |
| IV-3 | $CH_3$ | $C_2H_5$ | [3-methyl-2,5-dichlorothiophene] | $n_D^{20}$: 1.5321 |

*Same as footnote Table 1

USE EXAMPLES

The compound shown below was employed as the comparison substance in the use examples which follow:

$$\begin{array}{l} CH_2-NH-CS-S \\ \phantom{CH_2-NH-CS-S}\diagdown \\ \phantom{CH_2-NH-CS-SSSS}Zn \\ \phantom{CH_2-NH-CS-S}\diagup \\ CH_2-NH-CS-S \end{array} \quad (A)$$

zinc ethylene-1,2-bis-(dithiocarbamate)

EXAMPLE A

Phytophthora Test (tomato)/protective

Solvent: 4.7 parts by weight of acetone
Emulsifier: 0.3 parts by weight alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet 100% relative atmospheric humidity and at about 20° C.

Evaluation is carried out 3 days after the inoculation.

In this test, a clearly superior activity compared with the prior art is shown, for example, by the compounds according to preparation Examples 1, 5, 58, 68, 102, 103, 140.

EXAMPLE B

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 3, 27, 43, 104, 110, 115, 116, 118, 119 and 132.

EXAMPLE C

Pyricularia test (rice)/protective

Solvent: 12.5 parts by weight of acetone
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 5, 47, 67, 101, 103, 104, 106, 116, 118, 120, 123, 126, 127, 129, 140, 150 and 153.

EXAMPLE D

Pyricularia test (rice)/systemic

Solvent: 12.5 parts by weight of acetone
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 5, 7, 8, 14, 15, 16, 150 and 153.

It is understood that the specification and examples are illustrative but not limitative of the present invention and that other embodiments within the spirit and scope of the invention will suggest themselves to those skilled in the art.

What is claimed is:

1. A substituted pyrazolin-5-one of the formula $$\begin{array}{c} N = \phantom{x}R^1 \\ | \phantom{xxxx} \diagdown \\ N \phantom{xxxxx} \diagdown N-O-CH_2-Het \\ R^2 \diagup \phantom{xx} \| \\ \phantom{xxxxxx} O \end{array}$$

in which
$R^1$ and $R^2$ independently of one another in each case represent hydrogen, methyl, ethyl, n- or i-propyl, n-, i-, or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represent 1,1-dioxotetrahydrothien-3-yl, or represent phenyl or benzyl which is optionally mono-, di- or trisubstituted by identical or different substituents selected from the group consisting of fluorine, chlorine, bromine, iodine, cyano, nitro, hydroxyl, methyl, ethyl, n- or i-propyl, n-, i-, s- or t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl and Het represents a heterocyclic radical of the formula

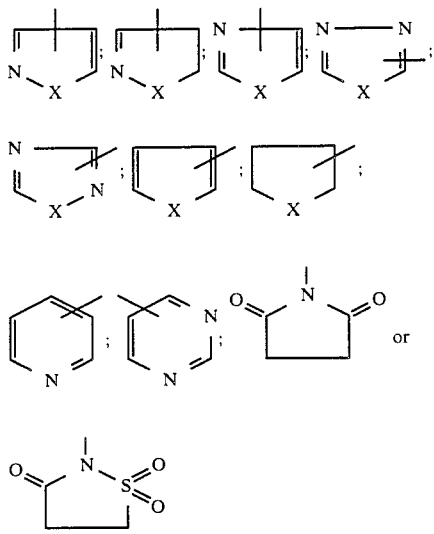

which is optionally mono-, di- or trisubstituted by identical or different substituents and optionally benzo-fused, when present the substituents in each case being: fluorine, chlorine, bromine, methyl, ethyl, n- or i-propyl, n-, i-, s- or t-butyl, methoxy, ethoxy, trifluoromethyl and phenyl which is optionally mono-, di- or trisubstituted by identical or different substituents from the group consisting of chlorine, nitro, methyl and/or methoxy and wherein X in each case represents oxygen or sulphur.

2. A compound according to claim 1, wherein such compound is 1-allyl-3-methyl-4-[(3-methylisoxazol-5-yl)-methoximino]-pyrazolin-5-one of the formula

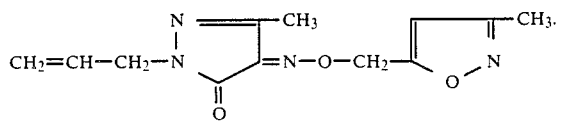

3. A compound according to claim 1, wherein such compound is 3-methyl-4-[3-methylisoxazol-5-yl)-methoximino]-1-phenyl-pyrazolin-5-one of the formula

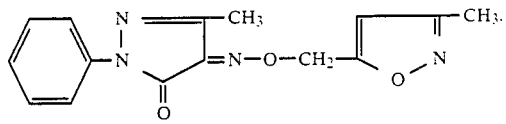

4. A compound according to claim 1, wherein such compound is 4-[(3-p-chlorophenyl-isoxazol-5-yl)-methoximino]-pyrazolin-5-one of the formula

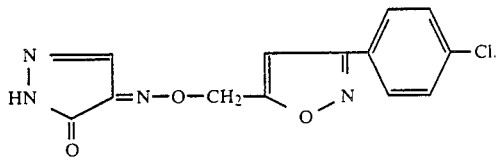

5. A compound according to claim 1, wherein such compound is 4-[(4,5-benzoisoxazol-2-yl)-methoximino]-1-cyanoethyl-pyrazolin-5-one of the formula

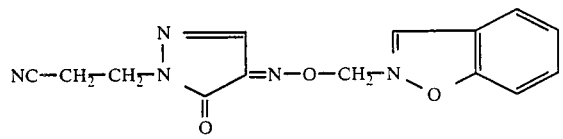

6. A compound according to claim 1, wherein such compound is 4-[(5-chloro-thien-2-yl)-methoximino]-3-methyl-pyrazolin-5-one of the formula

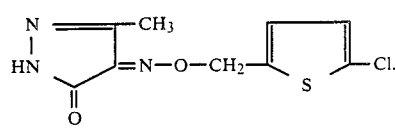

7. A compound according to claim 1, wherein such compound is 4-[(5-chloro-thien-2-yl)-methoximino]-1-cyanoethyl-3-methyl-pyrazolin-5-one of the formula

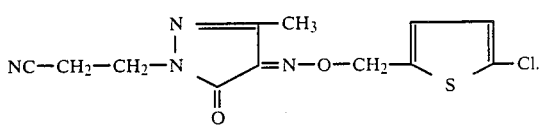

8. A compound according to claim 1, wherein such compound is 4-[(5-chloro-thien-2-yl)-methoximino]-1-hydroxyethyl-3-methyl-pyrazolin-5-one of the formula

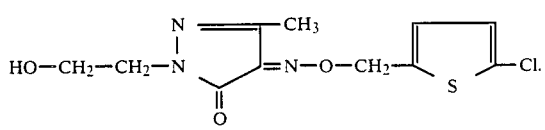

9. A fungicidal and bactericidal composition comprising a fungicidally and bactericially effective amount of a compound according to claim 1 and a diluent.

10. A method of combating fungi or bacteria which comprises applying to such fungi or bacteria or a habitat thereof a fungicidally or bactericidally effective amount of a compound according to claim 1.

11. The method according to claim 10, wherein such compound is 1-allyl-3-methyl-4-[(3-methylisoxazol-5-yl)-methoximino]-pyrazolin-5-one, 3-methyl-4-[3-methylisoxazol-5-yl)-methoxyimino]-1-phenyl-pyrazolin-5-one, 4-[(3-p-chlorophenyl-isoxazol-5-yl)-methoxyimino]-pyrazolin-5-one, 4-[(4,5-benzoisoxazol-2-yl)-methoximino]-1-cyano-ethyl-pyrazolin-5-one, 4-[(5-chloro-thien-2-yl)-methoximino]-3-methyl-pyrazolin-5-one, 4-[(5-chloro-thien-2-yl)-methoximino]-1-cyanoethyl-3-methyl-pyrazolin-5-one or 4-[(5-chloro-thien-2-yl)-methoximino]-1-hydroxyethyl-3-methyl-pyrazolin-5-one.

* * * * *